United States Patent [19]
Strike

[11] 3,931,299
[45] Jan. 6, 1976

[54] 9β-FORMYL PROSTAGLANDIN DERIVATIVES
[75] Inventor: Donald P. Strike, St. Davids, Pa.
[73] Assignee: American Home Products Corporation, New York, N.Y.
[22] Filed: Sept. 13, 1974
[21] Appl. No.: 505,803

[52] U.S. Cl.......... 260/514 D; 260/468 D; 424/305; 424/317
[51] Int. Cl.² .................. C07C 61/38; C07C 69/71
[58] Field of Search .................... 260/408 D, 514 D

[56] References Cited
OTHER PUBLICATIONS
Harrison et al., Tet. Lett. 5151 (1972).

Primary Examiner—Robert Gerstl
Attorney, Agent, or Firm—Robert Wiser

[57] ABSTRACT

Derivatives of 11-deoxy-$PGE_1$ and 11-deoxy-$PGE_2$ are prepared. These new compounds not heretofore found in nature possess various pharmacological activities, one of which is bronchodilation.

3 Claims, 1 Drawing Figure

9β-FORMYL PROSTAGLANDIN DERIVATIVES

BACKGROUND OF THE INVENTION

The prostaglandins are a group of hormone-like substances which may be viewed as derivatives of prostanoic acid. Several prostaglandins are found widely distributed in mammalian tissue and have been isolated from this source. These prostaglandins have been shown to possess a variety of biological properties such as broncho-dilation and the ability to reduce gastric secretion.

The present invention concerns $PGE_1$ and $PGE_2$ derivatives in which the 11-position (using the prostanoic acid numbering system) is a methylene group, i.e. the 11-hydroxyl group normally present in $PGE_1$ and $PGE_2$ has been removed and is replaced with hydrogen. The preparation of the parent molecules of this series, 11-deoxy-$PGE_1$ and 11-deoxy-$PGE_2$, is reported in J. Org. Chem. 38, 951 (1973).

SUMMARY OF THE INVENTION

The invention sought to be patented in a first composition aspect resides in the concept of a chemical compound of the structure

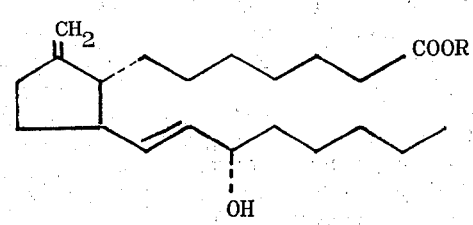

wherein R is hydrogen or alkyl of from 1 to 6 carbon atoms.

The tangible embodiments of the first composition aspect of the invention possess the inherent general physical properties of being clear to yellow oils, are substantially insoluble in water and are generally soluble in organic solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the first composition aspect of the invention possess the inherent applied use characteristic of exerting hypotensive effects upon administration to warm-blooded animals. These effects are evidenced by pharmacological evaluation according to standard test procedures.

The invention sought to be patented in a second composition aspect resides in the concept of a chemical compound of the structure

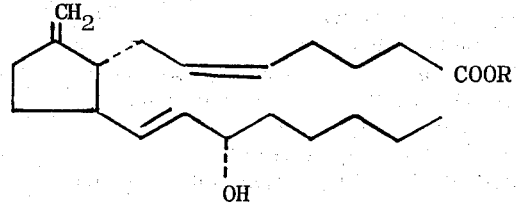

wherein R is H or alkyl of from 1 to 6 carbon atoms.

The tangible embodiments of the second composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the second composition aspect of the invention possess the inherent applied use characteristic of exerting bronchodilating effects upon administration to warm-blooded animals as evidenced by pharmacological evaluation according to standard test procedures.

The invention sought to be patented in a third composition aspect resides in the concept of a chemical compound of the structure

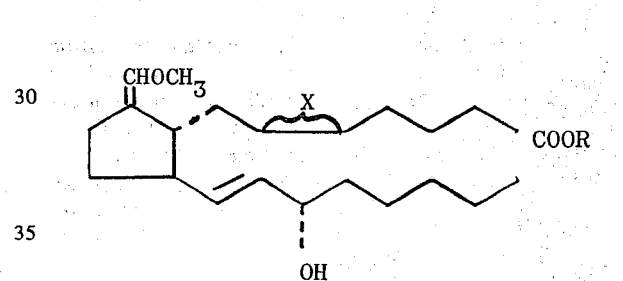

wherein
i. X is a single bond; or
ii. X is a cis double bond, and R is hydrogen or alkyl of from 1 to 6 carbon atoms.

The tangible embodiments of the third composition aspect of the invention possess the inherent general physical properties of being clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the third composition aspect of the invention possess the inherent applied use characteristic of being intermediates in the synthesis of the embodiments of the fourth composition aspect of the invention, and, in addition, when X is a cis double bond, are useful as intermediates in the synthesis of the embodiments of the fifth composition aspect of the invention.

The invention sought to be patented in a fourth composition aspect resides in the concept of a chemical compound of the structure

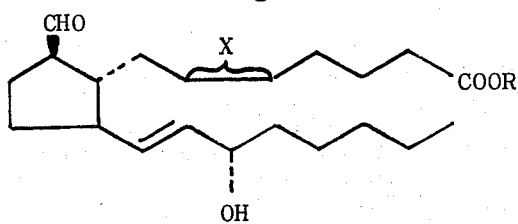

wherein
i. X is a single bond; or
ii. X is a cis double bond, and R is hydrogen or alkyl of from 1 to 6 carbon atoms.

The tangible embodiments of the fourth composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the fourth composition aspect of the invention possess the inherent applied use characteristic of exerting bronchodilating and hypotensive effects upon administration to warm-blooded animals as evidenced by pharmacological evaluation according to standard test procedures, and, in addition, when X is a cis double bond, are useful as intermediates in the synthesis of the embodiments of the fifth composition aspect of the invention.

The invention sought to be patented in a fifth composition aspect resides in the concept of a chemical compound of the structure

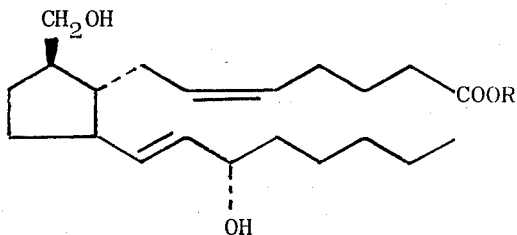

wherein R is hydrogen or alkyl of from 1 to 6 carbon atoms.

The tangible embodiments of the fifth composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infra-red, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the fifth composition aspect of the invention possess the inherent applied use characteristic of exerting hypotensive effects upon administration to warm-blooded animals as evidenced by pharmacological evaluation according to standard test procedures.

DESCRIPTION OF THE PREFERRED EMBODIMENTS

Figure 1:
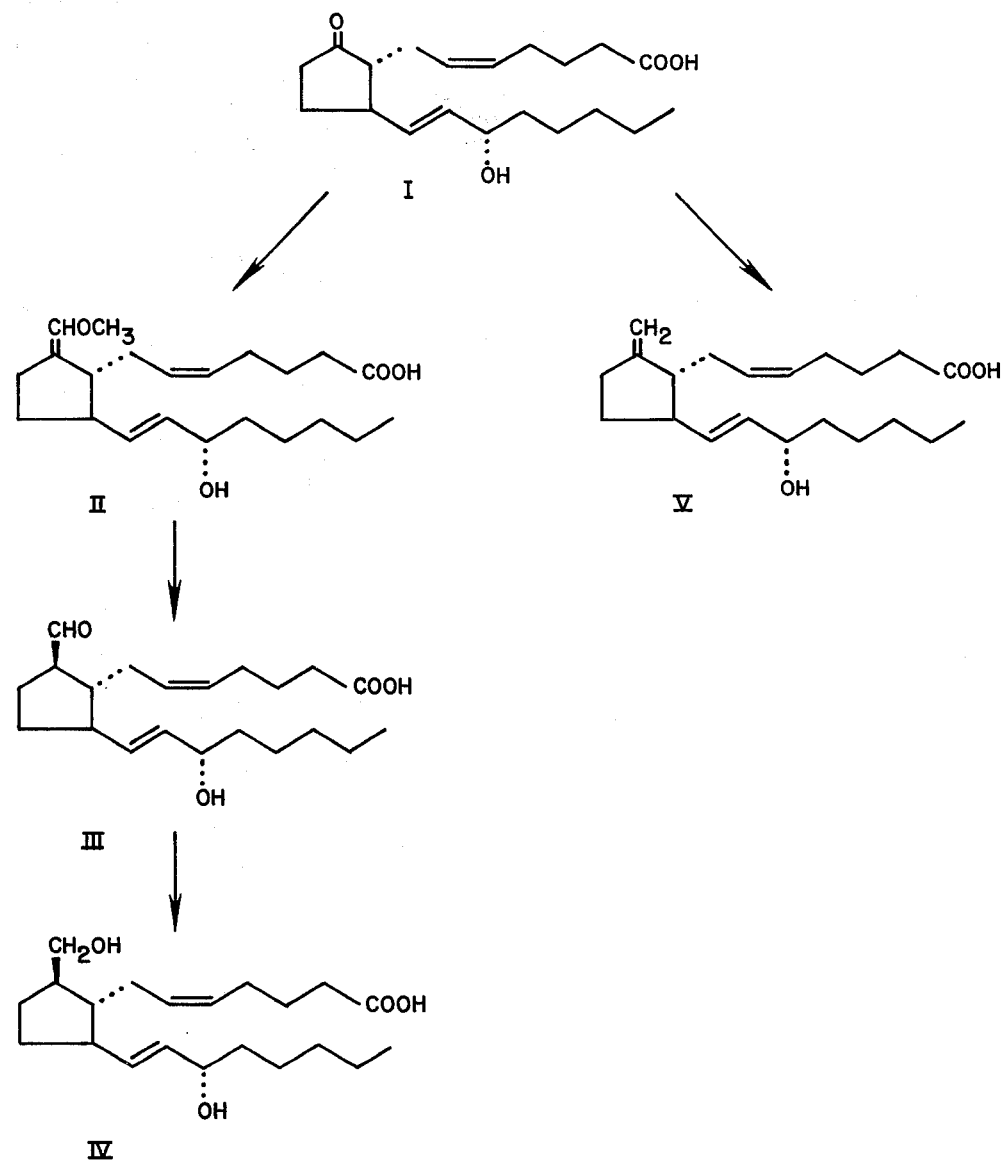

In describing the synthesis of the compositions of the invention, reference will be made to FIG. 1, wherein is illustrated the preparation of specific embodiments of the invention, and wherein the formulae representing the various aspects of the invention are assigned Roman numerals for purposes of identification. Additionally, in order to designate the stereochemistry of various substituents on the prostaglandin skeleton, different types of lines are utilized when representing the bonds of said substituents. Thus, with reference to the plane of paper, when a dashed line (----) is used, the substituent will be understood to be in the $\alpha$ (down) configuration; and when a heavy line (—) is used, the substituent will be understood to be in the $\beta$ (up) configuration. For purposes of convenience, the formulae in FIG. 1 are all free carboxylic acids; however, it will be obvious to those skilled in the art that these free acids may readily be esterified as for example with diazomethane, or with an alkanol and the proper catalyst. These esters are considered to be full equivalents to the free acids for the purposes of the invention. Finally, the use of specific embodiments in FIG. 1 to illustrate the invention is merely descriptive and is not intended to delimit the scope of the invention.

The starting materials for the synthesis of the compounds of the invention are 11-deoxy-PGE$_1$ (5,6-dihydro-I) and 11-deoxy-PGE$_2$ (I) which may be prepared synthetically as described, for example, in J. Org. Chem., 38, 951 (1973). Referring now to FIG. 1, 11-deoxy-PGE$_2$ (I) may first be reacted with the Wittig reagent derived from methoxymethyl-triphenylphosphonium chloride producing the vinyl ether II. This Wittig reaction has been found to proceed efficiently using sodium hydride-dimethylsulfoxide (Dimsylsodium, see, for example, Fieser and Fieser, Reagents for Organic Synthesis, Vol. I, Pg. 310, John Wiley and Sons, Inc., New York, 1967) as the base-solvent reagents. The vinyl ether function of II may next be hydrolyzed, with, for example, hydrochloric acid in tetrahydrofuran, producing the aldehyde III. Finally, reduction of the aldehyde function of III, with, for example, sodium borohydride in methanol, produces the primary alcohol IV.

Alternatively, the compound I may be reacted with the Wittig reagent derived from methyl-triphenylphosphonium bromide producing the methylene compound V. This Wittig reaction has been found to proceed efficiently using Dimsylsodium in dimethylsulfoxide as the base-solvent reagents.

Alternatively, if 11-deoxy-PGE$_1$ (5,6-dihydro-I) is used as starting material in the reaction sequence described above, the 5,6-dihydro analogs of II, III and V will be produced.

Various compounds of the invention bear carboxyl groups and can be readily converted to their respective alkali metal salts or a salt of a pharmacologically acceptable cation derived from ammonia or a basic amine. All such salts are full equivalents of the subject matter particularly claimed.

In using the compounds of the invention to produce bronchodilating effects in warm-blooded animals, they may be administered in a variety of dosage forms: oral, injectable, and aerosol inhalation. Aerosol inhalation is a preferred method because of its rapid onset of action, great potency, and specificity of action. The particular dosage to obtain the bronchodilating effect will vary with the particular compound employed, the particular animal involved, and the degree of bronchodilation desired. In the guinea pig, by aerosol inhalation, the dose to produce bronchodilation is from about 0.15 micrograms to about 100 micrograms, and preferably from about 0.15 to about 50 micrograms. The bronchodilation produced upon aerosol inhalation can be observed by the method of Rosenthale et al., J. Pharmacol. Exp. Ther., 178, 541 (1971).

Using this procedure, the following results were obtained.

| Compound | Dose ($\mu$g) | Percent inhibition of the bronchoconstricting effects of a standard dose of acetylcholine |
|---|---|---|
| 7-(2$\beta$-[(3S)-3-hydroxy-trans-1-octenyl]-5-methylene-1$\alpha$-cyclopentyl)-cis-5-heptenoic acid | 1.5 | 46 |
| 7-(5$\beta$-formyl-2$\beta$-[(3S)-3-hydroxy-trans-1-octenyl]-1$\alpha$-cyclopentyl)-cis-5-heptenoic acid | 1.5 | 55 |
| 5$\beta$-formyl-2$\beta$-([3S]-3-hydroxy-trans-1-octenyl-1$\alpha$-cyclopentane heptanoic acid | 0.15 | 36 |

In the use of the compounds of the invention to produce hypotensive effects in warm-blooded animals, administration by the injectable route is preferred, preferably the intravenous route.

Thus in the anesthetized dog by the intravenous route the dose to produce hypotension is from about 1 $\mu$g/kg. to about 200 $\mu$g/kg. and preferably from about 10 $\mu$g/kg. to about 100 $\mu$g/kg.

Using this procedure the following results were obtained.

| Compound | Dose ($\mu$g/kg.) | $\Delta$b.p. (mm. Hg) |
|---|---|---|
| 2$\beta$-([3S]-3-hydroxy-trans-1-octenyl)-5-methylene-1$\alpha$-cyclopentaneheptanoic acid | 100 | −32 |
| 7-(5$\beta$-formyl-2$\beta$-[(3S)-3-hydroxy-trans-1-octenyl]-1$\alpha$-cyclopentyl)-cis-5-heptenoic acid | 10 | −17 |
| 7-(5$\beta$-hydroxymethyl-2$\beta$-[(3S)-3-hydroxy-trans-1-octenyl]-1$\alpha$-cyclopentyl)-cis-5-heptenoic acid | 100 | −27 |
| 5$\beta$-formyl-2$\beta$-([3S]-3-hydroxy-trans-1-octenyl)-1$\alpha$-cyclopentane heptanoic acid | 100 | −27 |

The following examples further illustrate the best mode contemplated by the inventor for the practice of the invention.

EXAMPLE 1

7-[2$\beta$-((3S)-3-Hydroxy-Trans-1-Octenyl)-5-Methoxymethylene-1$\alpha$-Cyclopentyl]-Cis-5-Heptenoic Acid
(II)

Wash 1.44 g. of 50% sodium hydride-oil dispersion with pentane, decant and treat the sodium hydride with 30 ml. of dimethyl sulfoxide at 75°–80° for ¾ hr. under nitrogen. Cool to 25° and add a solution of 10.26 g. of methoxymethyl-triphenyl-phosphonium chloride in 60 ml. of dimethyl sulfoxide. After stirring for 10 minutes at 25°, add a solution of 1.0 g. of 7-[2$\beta$-((3S)-3-hydroxy-trans-1-octenyl)-5-oxo-1$\alpha$-cyclopentyl]-cis-5-heptenoic acid in 30 ml. of dimethyl sulfoxide and stir at 25° for 2.5 hours under nitrogen. Dilute the reaction mixture with water, acidify with acetic acid and extract with ether. After washing and drying, evaporate the ether extract and chromatograph the residue on silica with 20% ethyl acetate in hexane to obtain 0.65 g. of 7-[2$\beta$-((3S)-3-hydroxy-trans-1-octenyl)-5-methoxymethylene-1$\alpha$-cyclopentyl]-cis-5-heptenoic acid as an oil, $\lambda_{max}^{film}$ 3.0 (shoulder), 3.45, 5.85, 8.2, 8.9, 10.3 $\mu$. NMR: $\delta$ 6.62(s, 2, OH), 5.9 (m, 1, CH—OMe), 5.48 (m, 4, olefinic H), 4.08 (m, 1, 15-H), 3.55 (m, 3, OCH$_3$) ppm. Mass spectrum: M$^+$-H$_2$O at m/e 346.

EXAMPLE 2

2$\beta$-[(3S)-3-Hydroxy-Trans-1-Octenyl]-5-Methoxymethylene-1$\alpha$-Cyclopentane Heptanoic Acid
(5,6-Dihydro-II)

Wash 3.45 g. of 50% sodium hydride-oil dispersion twice with pentane, decant and treat the sodium hydride with 70 ml. of dimethyl sulfoxide at 75°–80° for 1.5 hr. under nitrogen. Cool to 25° and add a solution of 24.6 g. of methoxymethyl-triphenyl phosphonium chloride in 150 ml. of dimethyl sulfoxide. After stirring for 10 minutes at 25°, add a solution of 2.4 g. of 2$\beta$-[(3S)-3-hydroxy-trans-1-octenyl]-5-oxo-1$\alpha$-cyclopentane heptanoic acid in 70 ml. of dimethyl sulfoxide and stir at 25° for 2 hours under nitrogen. Dilute the reaction mixture with water, acidify with acetic acid and extract with ether. After washing and drying, evaporate the ether extract and chromatograph the residue on silica with 20% ethyl acetate in hexane to obtain 2.0 g. of 2$\beta$-[(3S)-3-hydroxy-trans-1-octenyl]-5-methoxymethylene-1$\alpha$-cyclopentane heptanoic acid as an oil, $\lambda_{max}^{film}$ 3.0 (shoulder), 3.45, 5.8, 8.15, 8.9, 10.3 $\mu$. NMR: $\delta$ 5.85 (m, 1, CH—OMe), 5.65 (m, 2, 13 and 14-H), 4.1 (m, 1, 15-H), 3.6 (m, 3, OCH$_3$) ppm. Mass spectrum: M$^+$ at m/e 366.

EXAMPLE 3

7-[5β-Formyl-2β-((3S)-3-Hydroxy-Trans-1-Octenyl)-1α-Cyclopentyl]-Cis-5-Heptenoic Acid (III)

Treat an ice-cold solution of 0.508 g. of 7-[2β-((3S)-3-hydroxy-trans-1-octenyl)-5-methoxy methylene-1α-cyclopentyl]-cis-5-heptenoic acid in 25 ml. of tetrahydrofuran with 1.0 ml. of hydrochloric acid and stir at 0° for 40 minutes under nitrogen. Dilute the reaction mixture with ether and, after washing and drying, evaporate the solvent and chromatograph the residue on silica with 20% ethyl acetate in hexane to obtain 0.176 g. of 7-[5β-formyl-2β-((3S)-3-hydroxy-trans-1-octenyl)-1α-cyclopentyl]-cis-5-heptenoic acid as an oil, $\lambda_{max}^{film}$ 3.0 (shoulder), 3.45, 5.8, 10.3 μ. NMR: δ 9.68 (d, 1, J=3, CHO), 6.9 (s, 2, OH), 5.5 (m, 4, olefinic), 4.12 (m, 1, 15-H) ppm. Mass spectrum: $M^+-H_2O$ at m/e 332.

EXAMPLE 4

5β-Formyl-2β-[(3S)-3-Hydroxy-Trans-1-Octenyl]-1α-Cyclopentane Heptanoic Acid (5,6-Dihydro-III)

An ice-cooled solution of 1.9 g. of 2β-[(3S)-3-hydroxy-trans-1-octenyl]-5-methoxymethylene-1α-cyclopentaneheptanoic acid in 100 ml. of tetrahydrofuran was treated with 4 ml. of hydrochloric acid and the mixture stirred at 0° for 1 hour under nitrogen. The mixture was diluted with ether, washed, dried, evaporated and the residue chromatographed on silica with 25% ethyl acetate in hexane to obtain 1.434 g. of 5β-formyl-2β-[(3S)-3-hydroxy-trans-1-octenyl]-1α-cyclopentane heptanoic acid as an oil, $\lambda_{max}^{film}$ 3.0 (shoulder), 3.4, 5,75, 6.8, 10.3 μ. NMR: δ 9.7 (d, 1, J=3, CHO), 6.4 (s, 2, OH), 5.55 (m, 2, 13 and 14-H), 4.1 (m, 1, 15-H) ppm. Mass spectrum: $M^+-H_2O$ at m/e 334.

EXAMPLE 5

7-[5β-Hydroxymethyl-2β-((3S)-3-Hydroxy-Trans-1-Octenyl)-1α-Cyclopentyl]-Cis-5-Heptenoic Acid (IV)

Treat an ice-cooled solution of 0.9 g. of 7-[5β-formyl-2β-((3S)-3-hydroxy-trans-1-octenyl)-1α-cyclopentyl]-cis-5-heptenoic acid in 70 ml. of methanol with an ice-cold solution of 2.7 g. of sodium borohydride in 150 ml. of methanol in portions over 5 minutes and stir at 0° for 15 minutes and at 25° for 0.5 hours. Concentrate the reaction mixture under vacuum at 40°, dilute the residue with water and extract with ether. After washing and drying, evaporate the ether extract and chromatograph the residue on silica with 50% ethyl acetate in hexane to obtain 0.57 g. of 7-[5β-hydroxymethyl-2β-((3-S)3-hydroxy-trans-1-octenyl)-1α-cyclopentyl]-cis-5-heptenoic acid as an oil, $\lambda_{max}^{film}$ 3.0, 3.4, 5.8, 8.1, 9.6, 10.3 μ. NMR: δ 5.52 (m, 4, olefinic), 4.12 (m, 1, 15-H), 3.55 (m, 2, CH₂O) ppm. Mass spectrum: $M^+$ at m/e 334.

EXAMPLE 6

7-[2β-((3S)-3-Hydroxy-Trans-1-Octenyl)-5-Methylene-1α-Cyclopentyl]-Cis-5-Heptenoic Acid (V)

Wash 0.72 g. of 50% sodium hydride-oil dispersion with pentane, decant and treat the sodium hydride with 15 ml. of dimethyl sulfoxide at 70°–80° for 0.5 hours under nitrogen. Cool the reaction mixture to 25° and add a solution of 5.355 g. of methyl-triphenyl phosphonium bromide in 35 ml. of dimethyl sulfoxide. After stirring for 10 minutes at 25°, add a solution of 0.5 g. of 7-[2β-((3S)-3-hydroxy-trans-1-octenyl)-5-oxo-1α-cyclopentyl]-cis-5-heptenoic acid in 10 ml. of dimethyl sulfoxide and stir at 25° for 1.5 hours under nitrogen. Dilute the reaction mixture with water, acidify with acetic acid and extract with ether. After washing and drying, evaporate the ether extract and chromatograph the residue on silica with 20% ethyl acetate in hexane to obtain 0.336 g. of 7-[2β-((3S)-3-hydroxy-trans-1-octenyl)-5-methylene-1α-cyclopentyl]-cis- 5-heptenoic acid as an oil, $\lambda_{max}^{film}$ 3.0 (shoulder), 3.4, 5.8, 8.0, 10.25, 11.3 μ. NMR: δ 6.72 (s, 2, OH), 5.65, (m, 2, 13 and 14-H), 4.95 (m, 2, methylene), 4.15 (m, 1, 15-H) ppm. Mass spectrum: $M^+$ at m/e 334, $M^+-H_2O$ at m/e 316.2398 (theory 316.2401).

EXAMPLE 7

2β-[(3S)-3-Hydroxy-Trans-1-Octenyl]-5-Methylene-1α-Cyclopentaneheptanoic Acid (5,6-Dihydro-V)

Sodium hydride-oil dispersion (1.12 g.) was washed with pentane and treated with 25 ml. of dimethylsulfoxide at 70°–80° for 0.75 hours under nitrogen. The solution was cooled, treated with 8.55 g. of methyl-triphenylphosphonium bromide in 50 ml. of dimethylsulfoxide and stirred at 25° for 10 minutes under nitrogen. A solution of 0.8 g. of 2β-[(3S)-3-hydroxy-trans-1-octenyl]-5-oxo-1α-cyclopentaneheptanoic acid in 20 ml. of dimethylsulfoxide was added and the mixture stirred at 25° for 3 hours. The reaction mixture was diluted with water, acidified with acetic acid and extracted with ether. After washing and drying, the extract was evaporated and the residue chromatographed on silica with 20% ethyl acetatehexane to obtain 0.625 g. of 2β-[(3S)-3-hydroxy-trans-1-octenyl]-5-methylene-1α-cyclopentaneheptanoic acid as an oil (solidified on standing), $\lambda_{max}^{film}$ 3.0 (shoulder), 3.4, 5.85, 10.35, 11.4 μ. NMR: δ 6.32 (s, 2, OH), 5.58 (m, 2, 13 and 14-H), 4.88 m, 2, methylene H), 4.10 (m, 1, 15-H) ppm. Mass spectrum: $M^+$ at m/e 336.2699 (theory 336.2663).

The subject matter which the applicants regard as their invention is particularly pointed out and distinctly claimed as follows:

1. A chemical compound of the structure:

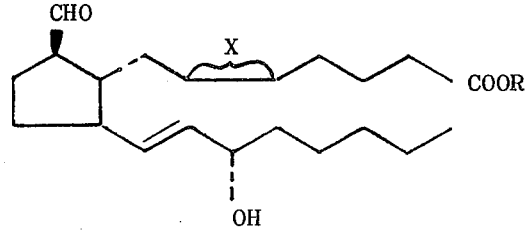

wherein
  i. X is a single bond; or
  ii. X is a cis double bond,
and R is hydrogen or alkyl of from 1 to 6 carbon atoms.

2. The compound of claim 1 wherein X is a single bond and R is hydrogen.

3. The compound of claim 1 wherein X is a cis double bond and R is hydrogen.

* * * * *